United States Patent [19]

Haber et al.

[11] Patent Number: 5,514,107
[45] Date of Patent: May 7, 1996

[54] SAFETY SYRINGE ADAPTER FOR CARTRIDGE-NEEDLE UNIT

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 194,362

[22] Filed: Feb. 10, 1994

[51] Int. Cl.⁶ .................................................. A61M 5/32
[52] U.S. Cl. .................... 604/197; 604/232; 604/192; 128/763
[58] Field of Search ...................... 604/192–197, 604/232, 233, 110, 218, 234, 187, 220, 228; 128/919, 763; 433/89, 90

[56] References Cited

U.S. PATENT DOCUMENTS

| | | | |
|---|---|---|---|
| 4,664,653 | 5/1987 | Sagstetter et al. | 604/197 |
| 4,664,654 | 5/1987 | Strauss | 604/198 |
| 4,826,489 | 5/1989 | Haber et al. | 604/195 |
| 4,834,717 | 5/1989 | Haber et al. | 604/232 |
| 4,846,808 | 7/1989 | Haber et al. | 604/195 |
| 4,850,961 | 7/1989 | Wanderer et al. | 604/53 |
| 4,892,107 | 1/1990 | Haber | 128/763 |
| 4,931,040 | 6/1990 | Haber et al. | |
| 4,944,723 | 7/1990 | Haber et al. | |
| 4,957,490 | 9/1990 | Byrne et al. | 604/197 |
| 5,045,066 | 9/1991 | Scheuble et al. | 604/198 |
| 5,067,490 | 10/1991 | Haber | |
| 5,067,948 | 11/1991 | Haber et al. | 604/213 |
| 5,084,017 | 1/1992 | Maffetone | 604/228 |
| 5,141,500 | 8/1992 | Hake | 604/198 |
| 5,232,457 | 8/1993 | Grim | 604/195 |

FOREIGN PATENT DOCUMENTS 0467173   1/1992   European Pat. Off. ............ 604/198

*Primary Examiner*—C. Fred Rosenbaum
*Assistant Examiner*—V. Alexander
*Attorney, Agent, or Firm*—Townsend and Townsend and Crew

[57] ABSTRACT

A safety syringe adapter (4) has a hollow body (26) sized to house a cartridge-needle unit (6) to which a carrier (24) is fixed. The cartridge-needle unit and carrier therewith are movable from a use position, with the needle tip (58) exposed, to a safe disposal position, with the needle tip within the body. A stem assembly (28) has an elongate stem (60) and a coaxial tubular stem extension (64) and is movable to a post-injection position, at which the stem extension becomes secured to the carrier. Pulling the stem assembly proximally causes the cartridge-needle unit to move to its safe-disposal position so the needle tip is within the body for safe disposal.

15 Claims, 6 Drawing Sheets

5,514,107

SAFETY SYRINGE ADAPTER FOR CARTRIDGE-NEEDLE UNIT

BACKGROUND OF THE INVENTION

Various medications are often supplied using cartridge-needle units and a syringe adapter. The cartridge-needle units include a barrel having a piston at one end and a needle assembly at the other with the pharmaceutical to be injected housed within the syringe barrel between the piston and the needle assembly. The adapter typically includes a hollow body sized to hold the barrel of the cartridge-needle unit and a stem designed to engage the piston. The cartridge-needle unit is mounted within the adapter body and the injection is given. After use, the cartridge-needle unit is disposed of while the body and stem of the adapter can be reused.

One of the problems with health care delivery is risk of infectious diseases being spread through accidents, especially needle sticks, with used syringes. There have been many attempts to create safety syringes in which the needle is either manually or automatically drawn into the barrel or other housing of the syringe after use. However, these designs have not fully addressed the problems associated with the safe disposal of conventional cartridge-needle units after use.

SUMMARY OF THE INVENTION

The present invention is directed to a safety syringe adapter for use with a conventional cartridge-needle unit which has few parts, is inexpensive to produce and is easy to use.

The safety syringe adapter is designed for use with a cartridge-needle unit of the type having a barrel housing a piston and a needle assembly at the distal end of the barrel. The adapter includes a hollow body having open proximal and distal ends and is sized to house the cartridge-needle unit therein. A carrier is securable to the distal end of the cartridge-needle unit and is movable, together with the cartridge-needle unit, within the body from a distal position, with the tip of the needle exterior of the body, to a proximal position, with the needle tip positioned within the body.

A stem assembly includes an elongate stem, which engages the piston, and a stem extension, which extends parallel to the stem. The stem assembly is movable in a distal direction from a pre-use position, prior to an injection, to a post-injection position, after an injection, at which point the stem extension becomes secured to the carrier. Pulling the stem assembly in a proximal direction causes the carrier and cartridge-needle unit therewith to move in a proximal direction as well until the stem assembly reaches a safe disposal position. At this point the tip of the needle is positioned within the body and the carrier becomes secured to the body at the proximal position. Further proximal movement of the stem extension can be prevented, such as by engagement of radially inwardly extending teeth carried by the body with a locking region on the stem extension. The used syringe can now be disposed of safely.

One of the primary advantages of the invention is that it is adapted for use with conventional cartridge-needle units, such as that made by Wyeth Labs, Inc. of Philadelphia, Pa. No specially designed ampules or cartridge-needle units need be used. Also, the user needs to simply pull on the stem assembly after the injection has been given to pull the needle into the hollow body and lock the syringe into its safe disposal condition. No twisting or separate manipulation of buttons or latches needs to be accomplished. A further advantage of the invention is that it can be made using only three parts, in addition to the cartridge-needle unit. It can thus be relatively inexpensive to produce and suitable for use as a disposable adapter.

Other features and advantages of the invention will appear from the following descriptions in which the preferred embodiment has been set forth in detail in conjunction with the accompanying drawings.

DESCRIPTION OF THE PREFERRED EMBODIMENT

Figure 1:
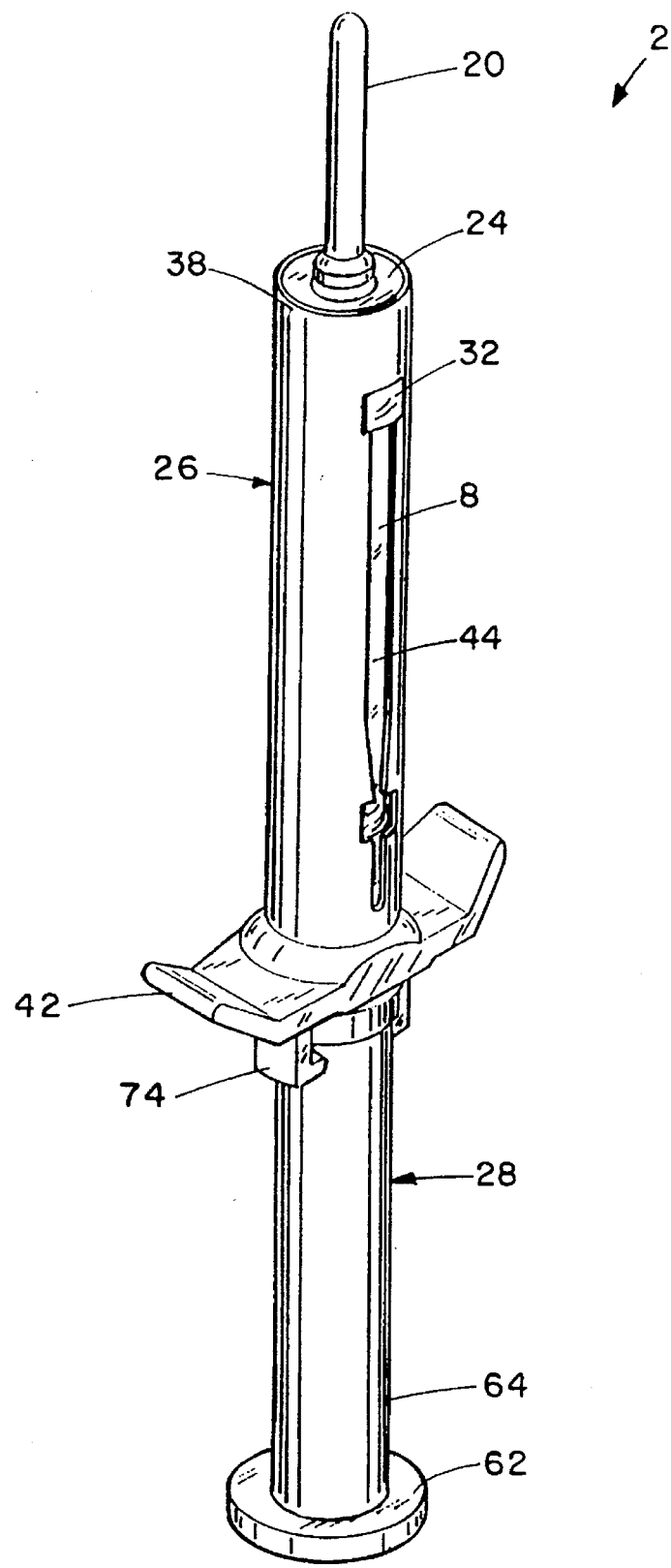
FIG. 1 is an isometric view of a safety syringe made according to the invention in its pre-use or as-shipped condition.
Figure 2:
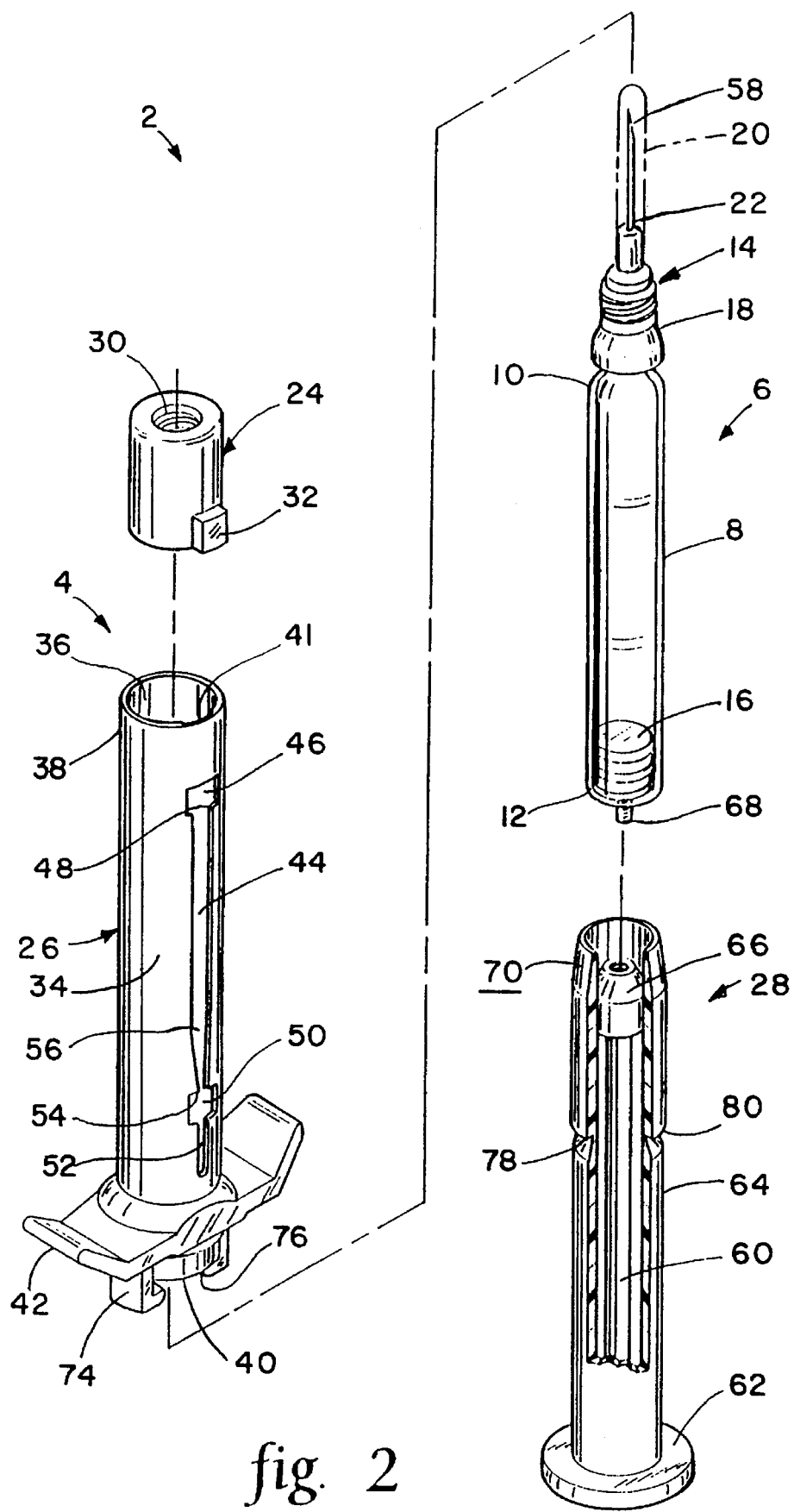
FIG. 2 is an exploded isometric view of the syringe of FIG. 1.
Figure 3:
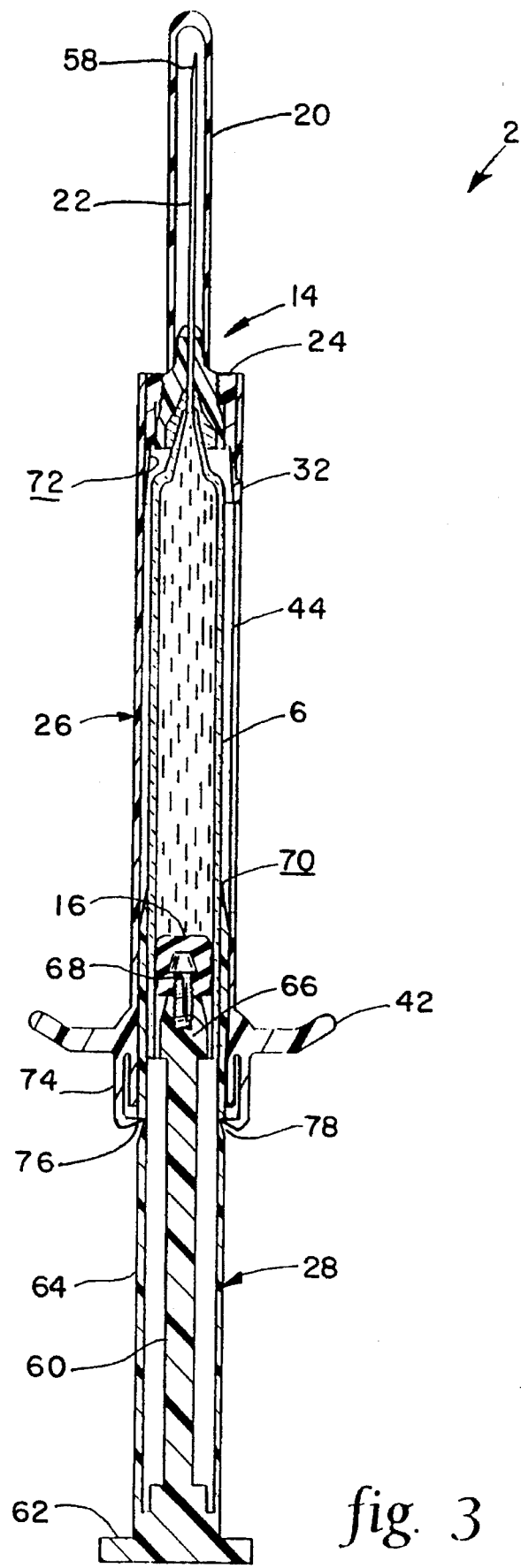
FIG. 3 is a cross-sectional view of the syringe of FIG. 1 in the pre-use or as-shipped condition, with the cartridge-needle unit in its use position, the stem assembly in its pre-use position and the carrier in its distal position, the cutting plane passing axially along the slot in the hollow body and then rotating 90° near the proximal end of the slot to pass through the finger ledges and spring tabs.
Figure 4:
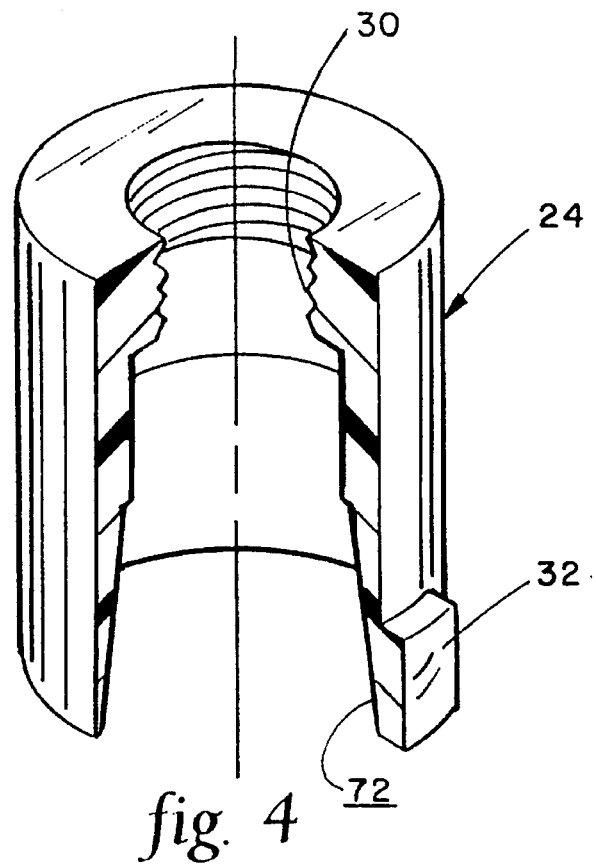
FIG. 4 is an enlarged view of the carrier of FIG. 2 with a section broken away to show the interior.

FIGS. 1–3 illustrate a safety syringe 2 including a safety syringe adapter 4 and a cartridge-needle unit 6. Cartridge-needle unit 6 can be a commercially available cartridge-needle unit such as made by Wyeth Labs, Inc. of Philadelphia, Pa. Cartridge-needle unit 6 includes a barrel 8 having a distal end 10, a proximal end 12, a needle assembly 14 at distal end 10 and a piston 16 housed within barrel 8 at proximal end 12. Cartridge-needle unit 6 is filled with a pharmaceutical or other liquid. In the preferred embodiment, needle assembly 14 has external threads 8 and a removable safety sheath 20 covering a needle cannula 2.

Adapter 4 includes, in the preferred embodiment, three parts: a carrier 24, a hollow body 26 and a stem assembly 28. Carrier 24 is generally cylindrical in shape and has internal threads 30 sized to engage external threads 18 formed on needle assembly 14 to create a cartridge needle unit assembly. Carrier 24 also includes a radially outwardly extending boss 32 which acts as a guide element within body 26 as discussed below.

Body 26 has a generally cylindrical side wall 34 defining a hollow interior 36 extending from an open distal end 38 to an open proximal end 40. The initial entry of carrier 24 into interior 36 of side wall 34 through end 38 is accommodated by a tapering entrance ramp 41 along which boss 32 slides. A pair of finger ledges 42 extend radially outwardly from body 26 at proximal end 40.

Side wall 34 has an axially extending slot 44 within which boss 32 slides. Slot 44 extends from a distal retaining region 46, which is defined in part by relatively small retaining shoulders 48, through a proximal locking region 50 and on to a slot extension 52. Proximal locking region 50 is defined in part by relatively large locking shoulders 54 which are created by a narrowing slot portion 56 adjacent proximal locking region 50. As will be discussed in more detail below, boss 32 fits within and is normally retained within distal retaining region 46 when syringe 2 is in its pre-use condition of FIGS. 1 and 3 by virtue of retaining shoulder 48. However, upon exertion of a moderate proximally directed force, boss 32 can be moved proximally (that is towards finger ledges 42) within slot 44 by expanding slot 44. Continued proximal movement causes boss 32 to engage within proximal locking region 50. However, since locking shoulders 54 are much larger than retaining shoulders 48, distal movement of carrier 24 is effectively not possible. The lateral deflection of side wall 34 as boss 32 passes within narrowing slot portion 56 is accommodated by the provision of slot extension 52. The configuration of boss 32 and of slot 44 effectively prevents distal movement of carrier 24 when boss 32 is in distal retaining region 46 and both distal and proximal movement of carrier 24 when boss 32 is within proximal locking region 50.

Figure 5:
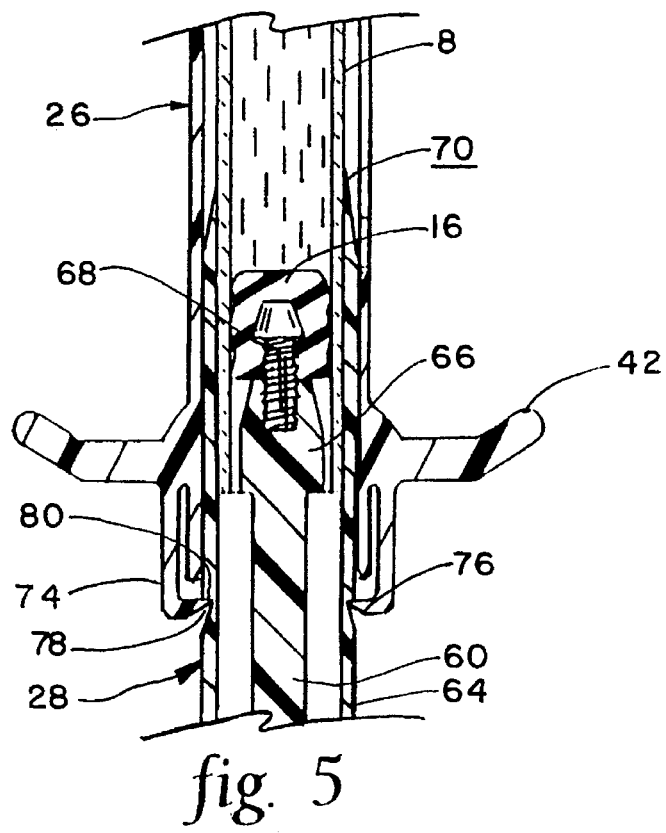
FIG. 5 is an enlarged cross-sectional view of a portion of the syringe of FIG. 3.
Figure 6:
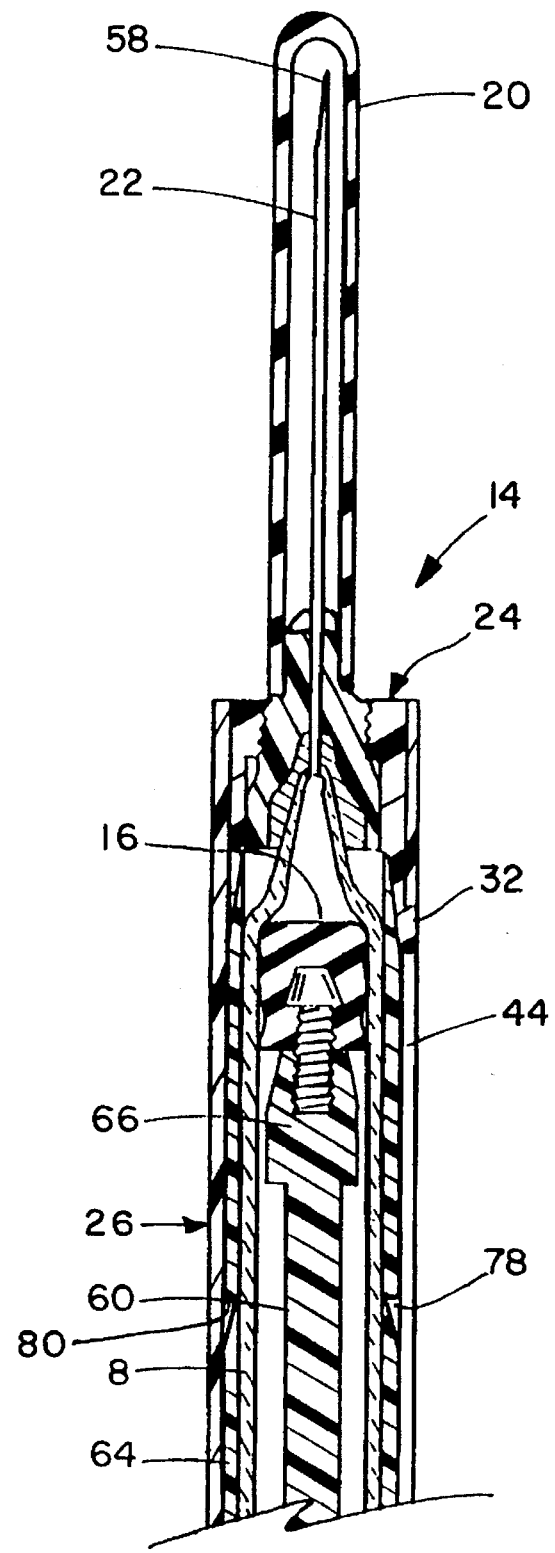
FIG. 6 is an enlarged view of the distal portion of the syringe of FIG. 3 but with the stem assembly in its post-injection position and engaged with the carrier.
Figure 7:
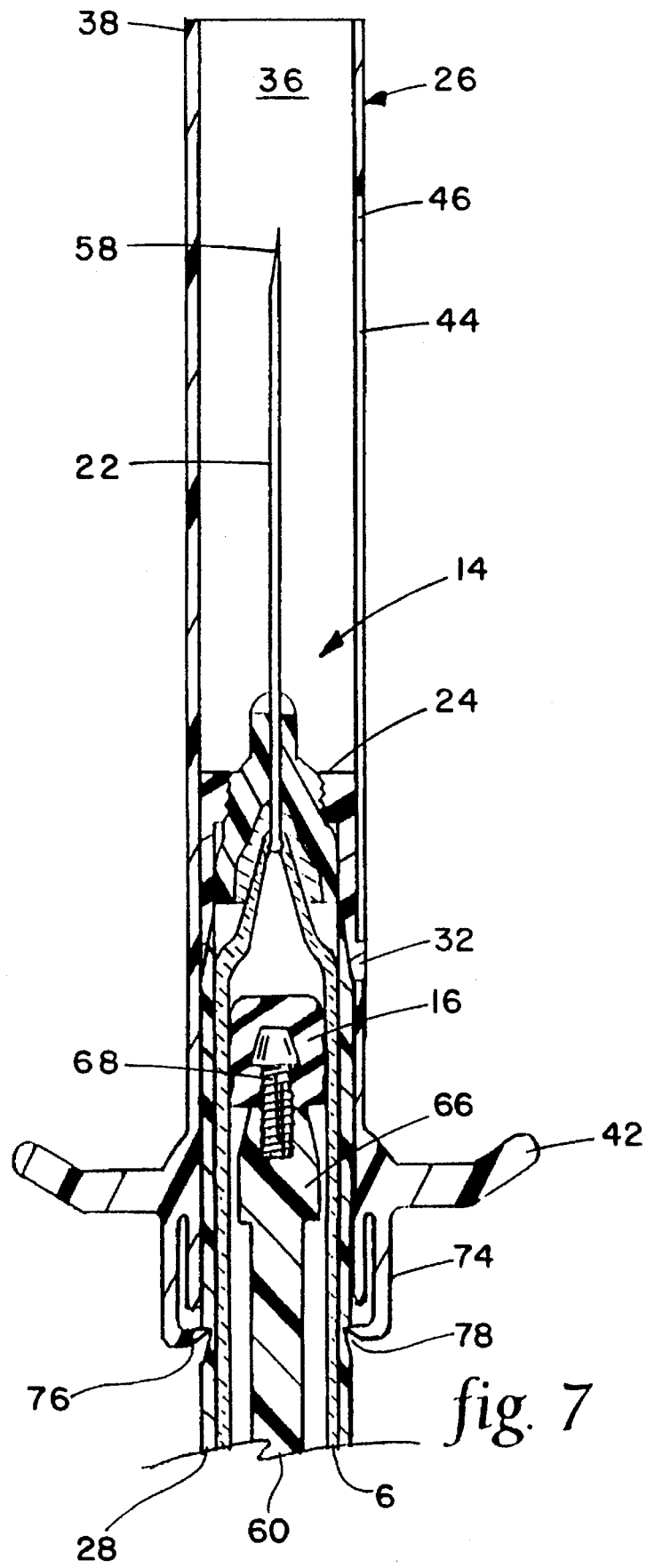
FIG. 7 is an enlarged view of a portion of the syringe of FIG. 3 but with the syringe in its safe-disposal condition with the stem assembly in its safe disposal position, the carrier in its proximal position and the needle tip positioned within the hollow body.

As shown in FIG. 3, cartridge-needle unit 6 is secured to carrier 24 through the engagement of threads 18, 30 so that cartridge-needle unit 6 moves with carrier 24 as carried 24 moves from its distal position, with boss 32 engaged within region 46, see FIGS. 3 and 5, to its proximal position, with boss 32 engaged within region 50, see FIG. 7. As shown in FIGS. 1, 3 and 6, the tip 58 of needle 22 is external of body 26 when carrier 24 is in its distal position and cartridge-needle unit 6 is in its use position. Tip 58, see FIG. 7, is positioned within body 26 when boss 32 is in its proximal position and cartridge-needle unit 6 is in its safe-disposal position.

This movement of carrier 24 and cartridge-needle unit 6 is accomplished by movement of stem assembly 28. Stem assembly 28 includes a stem 60 extending from a thumb pad 62 and a stem extension 64 also extending from thumb pad 62 coaxially with and surrounding stem 60. As shown in FIG. 3, the tip 66 of stem 60 is threaded to a threaded stud 68 extending from piston 16, as is conventional.

Stem extension 64 is generally cylindrical and fits between barrel 8 and side wall 34 so as to stabilize both cartridge-needle unit 6 and stem 60. Stem assembly 28 is moved from its pre-use or as-shipped position of FIG. 3 to its post-injection position of FIG. 6 by the user pressing on thumb pad 62 while grasping finger ledges 42, as is conventional. At the end of this movement, as shown in FIG. 6, an outer tapered surface 70 formed at the distal end of stem extension 64 frictionally engages a complementary inner tapered surface 72 of carrier 24. The frictional engagement between surfaces 70, 72 is sufficient so that when the user subsequently pulls on thumb pad 62 in a proximal direction, the frictional engagement overcomes the resistance of retaining shoulders 48, thus pulling carrier 24 and cartridge-needle unit 6 therewith in the proximal direction until boss 32 engages proximal locking region 50. At this point carrier 24 and cartridge-needle unit 6 are effectively locked within body 26 with tip 58 sheltered by side wall 34 of the body as shown in FIG. 7.

To prevent the inadvertent or unauthorized removal of stem assembly 28 from body 26, body 26 has a pair of spring tabs 74 with radially inwardly directed teeth 76 at open proximal end 40 of body 26. Teeth 76 are positioned to engage a tapered locking region 78 formed in stem extension 64. Region 78 is defined in part by a radially extending shoulder 80 which teeth 76 engage in the event of attempted complete removal of stem assembly 28 from body 26.

In the preferred embodiment, the pre-use and safe-disposal positions of stem assembly 28 relative to body 26 are the same proximal position as shown in FIGS. 3 and 7. However, stem assembly 28 could assume different proximal positions relative to body 26 if desired.

In use, syringe 2, in the pre-use condition in FIGS. 1 and 3, is selected and safety sheath 20 is removed. The injection is then given in a conventional manner by pressing on thumb pad 62 while grasping finger ledges 42. At the end of an injection, stem assembly 28 is in the post injection position of FIG. 6 so that surfaces 70, 72 frictionally engage. To prepare for disposal of syringe 2, thumb pad 62 is pulled in the proximal direction until stem assembly 28 is in its safe-disposal position and carrier 24 is in its proximal position, see FIG. 7, thus placing syringe 2 in its safe-disposal condition with needle tip 58 positioned within body 26. Used syringe 2 can then be safely disposed of.

In the preferred embodiment, components of safety syringe adapter 4 are made of suitable plastics, such as polycarbonate. It is preferable that the user be able to see the contents of cartridge-needle unit 6 so that body 26 and stem assembly 64, at least, are preferably made of transparent or clear material. In the preferred embodiment, stem assembly 64 is generally cylindrical; however, other elongate stem extension structures, such as the axially extending rods tied together at their distal ends with a circular ring, could be used. The engagement between stem extension 64 and carrier 24 can be other than a tapered friction fit. For example, detents, barbed elements, spring fingers or, threaded engagement elements could be used between stem extension 64 and carrier 24. Also, stem assembly 28 could be configured to become secured to proximal end 12 of barrel 8 when at its post-injection position rather than being secured to carrier 24. Locking carrier 24 in its proximal position could be accomplished using other catch elements; for example a one-way ratchet between carrier 24 and the inner surface of side wall 26, or an inwardly biased tooth extending into interior 36 from side wall 26 to catch on carrier 24, could be used. Carrier 24 could be secured to cartridge needle unit 6 other than by threads 18, 30; for example, carrier 24 could be configured to snap over and engage the shoulder of needle assembly 14 adjacent distal end 10 of barrel 8.

Other modifications and variations can be made to the disclosed embodiment without departing from the subject of the invention as defined in the following claims.

What is claimed is:

1. A safety syringe adapter comprising:

a cartridge-needle unit comprising a barrel, a piston housed within the barrel and a needle assembly at a distal end of the barrel, the needle assembly including a hollow needle having a tip a hollow body having open proximal and distal ends and having an interior sized to house the cartridge-needle unit therein;

a carrier, removably secured to the cartridge-needle unit to create a cartridge-needle unit assembly, the carrier being movable between a distal position, with the tip of the hollow needle exterior of the body, and a proximal position, with the tip of the hollow needle within the body;

a stem assembly having a stem engageable with the piston and a stem extension extending generally parallel to the stem, the stem extension integral with the stem and having a distal end housed within the interior of the hollow body between the hollow body and the barrel, the stem assembly movable in a distal direction from a pre-use position to a post-injection position and then in a proximal direction to a safe-disposal position;

means for coupling the distal end of the stem extension to the cartridge-needle unit assembly when the stem assembly is at the post-injection position so that moving the stem assembly to the safe-disposal position moves the carrier to its proximal position so the tip of the needle of the cartridge-needle unit is moved to be within the body; and means for locking the carrier at its proximal position for safe disposal.

2. The safety syringe adapter of claim 1 wherein the body has finger ledges at the proximal end thereof.

3. The safety syringe adapter of claim 1 further comprising means for preventing complete removal of the stem assembly from the interior of the body.

4. The safety syringe adapter of claim 3 wherein the removal preventing means includes a locking region defined by the stem assembly and spring tabs carried by the body having teeth sized and positioned to engage the locking region upon attempted complete removal of the stem assembly from the body.

5. The safety syringe adapter of claim 4 wherein the stem extension is a tubular member and the locking region is a recessed region formed in the tubular member, the recessed region partially defined by a generally radially extending shoulder.

6. The safety syringe adapter of claim 1 wherein the carrier is threadably securable to the needle assembly of the cartridge-needle unit.

7. The safety syringe adapter of claim 1 wherein the coupling means includes complementary mating tapering surfaces on the carrier and the stem extension to provide frictional coupling therebetween.

8. The safety syringe adapter of claim 1 wherein the carrier locking means includes a guide element on the carrier which engages an axially extending slot in the body, the slot having a distal retaining region and a proximal locking region, the guide element and the proximal locking region sized and configured so that when the guide element is housed within the proximal locking region, the guide element is effectively locked therein.

9. The safety syringe adapter of claim 1 wherein the stem extension is a tubular member made of transparent material.

10. The safety syringe adapter of claim 1 wherein the stem extension is tubular.

11. A safety syringe comprising:

a cartridge-needle unit including a barrel, a piston housed within the barrel and a needle assembly at a distal end of the barrel, the needle assembly including a hollow needle having a tip;

a hollow body having open proximal and distal ends, an interior sized to house the cartridge-needle unit therein and finger ledges at the proximal end thereof;

a carrier, secured to the cartridge-needle unit and movable between a distal position, with the tip of the hollow needle exterior of the body, and a proximal position, with the tip of the hollow needle within the body;

a stem assembly having a stem engageable with the piston and a tubular stem extension integral, circumscribing and coaxial with the stem, the stem assembly movable in a distal direction from a pre-use position to a post-injection position and then in a proximal direction to a safe-disposal position;

the stem extension and the carrier including complementary engagement surfaces which mate and become secured to one another only when the stem assembly is at the post-injection injection position so that moving the stem assembly to the safe-disposal position moves the carrier to its proximal position so the tip of the needle of the cartridge-needle unit is moved to be within the body;

means for locking the carrier at its proximal position for safe disposal; and means for preventing complete removal of the stem assembly from the interior of the body, the removal preventing means includes a locking region defined by the stem assembly and spring tabs carried by the body having teeth sized and positioned to engage the locking region upon attempted complete removal of the stem assembly from the body.

12. A safety syringe adapter comprising:

a cartridge-needle unit comprising a barrel, a piston housed within the barrel and a needle assembly at a distal end of the barrel, the needle assembly including a hollow needle cannula having a tip;

a body defining a hollow interior sized to house the cartridge-needle unit therein and an axis, the body having open proximal and distal ends and a sidewall with an axially extending slot formed in the sidewall, the slot having a distal retaining region and a proximal locking region;

a carrier mounted within the hollow interior, the carrier having a guide element sized to fit within and be guided by the slot as the carrier moves between a distal position, with the guide element removably retained within the retaining region, and a proximal position, with the guide element effectively locked within the locking region;

the carrier including an attachment element configured to permit the carrier and the cartridge-needle unit to be secured to one another so that the cartridge-needle unit moves between a use position, when the carrier is at the distal position with the tip of the needle cannula exterior of the body, and a safe disposal position, when the carrier is at the proximal position with the tip of the needle within the body;

a stem assembly including an elongate stem having a distal end engageable with the piston and a proximal end extending past the open proximal end of the body, the stem assembly movable in a distal direction from a pre-use position to a post-injection position; and the stem assembly also including a tubular stem extension extending from the proximal end of the stem and surrounding at least a portion of the stem, the stem extension including a distal end having a carrier engaging portion configured to become secured to the carrier when the stem assembly is at the post-injection position so that movement of the stem assembly from the post-injection position in the proximal direction to a safe-disposal position causes the cartridge-needle unit and carrier therewith to move to the safe disposal position and the tip of the needle to be positioned within the body.

13. A safety syringe adapter comprising:

a cartridge-needle unit comprising a barrel, a piston housed within the barrel and a needle assembly at a distal end of the barrel, the needle assembly including a hollow needle having a tip;

a hollow body having open proximal and distal ends and having an interior sized to house the cartridge-needle unit therein;

a carrier, removably secured to the cartridge-needle unit to create a cartridge-needle unit assembly, the carrier being movable between a distal position, with the tip of the hollow needle exterior of the body, and a proximal position, with the tip of the hollow needle within the body;

a stem assembly having a stem engageable with the piston and a tubular stem extension extending generally parallel to the stem, the tubular stem extension being coupled to the stem and the hollow body, the stem assembly movable in a distal direction from a pre-use position to a post-injection position and then in a proximal direction to a safe-disposal position;

means for coupling the stem extension to the cartridge-needle unit assembly when the stem assembly is at the post-injection position so that moving the stem assembly to the safe-disposal position moves the carrier to its proximal position so the tip of the needle of the cartridge-needle unit is moved to be within the body; and means for locking the carrier at its proximal position for safe disposal, the locking means comprising a guide element on the carrier which engages an axially extending slot in the body, the slot having a distal retaining region, a proximal locking region and an intermediate region therebetween, the guide element, the intermediate region and the proximal locking region being sized and configured so that when a sufficient proximal axial force is applied to the guide element, the guide element slides through the intermediate region into the proximal locking region and is effectively locked therein.

14. The safety syringe adapter of claim 13 wherein the intermediate region has opposing walls that taper towards each other from the distal retaining region to the proximal locking region, the guide element being sized to laterally deflect the opposing walls as the guide element slides through the intermediate region.

15. The safety syringe adapter of claim 14 wherein the slot further includes an axial extension proximal the proximal locking region to facilitate the lateral deflection of the opposing walls of the intermediate region.

* * * * *